United States Patent [19]
Voss et al.

[11] Patent Number: 5,595,178
[45] Date of Patent: Jan. 21, 1997

[54] SYSTEM, METHOD AND APPARATUS FOR TREATMENT OF DEGENERATIVE BONE

[75] Inventors: Joachim Voss, Munich; Werner Schwarze, Stockach-Hoppetenzell; Reiner Schultheiss, Salem-Mimmenhausen, all of Germany

[73] Assignee: HMT High Medical Technologies GmbH, Jena, Germany

[21] Appl. No.: 333,372

[22] Filed: Oct. 2, 1994

[51] Int. Cl.⁶ ..................................................... A61B 6/00
[52] U.S. Cl. ............................................ 128/653.1; 601/2
[58] Field of Search ........................... 128/653.1, 660.03; 601/2–4; 607/97

[56] References Cited

U.S. PATENT DOCUMENTS

| | | |
|---|---|---|
| 2,559,227 | 7/1961 | Reiber . |
| 4,905,671 | 3/1990 | Senge et al. ................................ 601/4 |
| 4,979,501 | 12/1990 | Valchanov et al. ......................... 601/2 |
| 5,178,135 | 1/1993 | Uchiyama et al. ................ 128/660.03 |
| 5,327,890 | 7/1994 | Matura et al. ........................ 128/653.1 |

FOREIGN PATENT DOCUMENTS

| | | |
|---|---|---|
| 0183236 | 6/1986 | European Pat. Off. . |
| 0450423 | 10/1991 | European Pat. Off. . |
| 2351247 | 8/1976 | Germany . |
| 4036981 | 5/1992 | Germany . |
| 4000362 | 11/1993 | Germany . |

*Primary Examiner*—Ruth S. Smith
*Attorney, Agent, or Firm*—Eugene E. Renz, Jr.

[57] ABSTRACT

A process for therapeutic treatment of changes in human or animal bones which cause a boundary surface gap with a width of less than 5 millimeters to form between the bone and an acoustically reflective body such as an implant, a tooth or a bone fragment. The process include a first step of locating the desired boundary surface gap by means of a locating device; next the body of the patient is exposed to acoustic shock waves through the surface of the skin after focusing the shock waves on the boundary surface gap. Vibrations are generated in the bone surfaces, the surfaces of the acoustically reflecting body, and at the gap by multiple reflections of the generated shock waves. The preferred device for carrying out the process uses a therapy head to generate and focus acoustic shock waves in a predetermined direction. The shock waves are conducted through the surface of the skin into the body of the patient by a coupling unit. An x-ray beam imaging system and two targets in which the patient and two targets are placed between the source and imaging system and the two targets are connected mechanically in a moveable manner to the therapy head so that the two targets may be rotated around at least two different axis in such as way that an imaginary line connecting the two targets always passes through the focal point of the shock waves.

2 Claims, 7 Drawing Sheets

FIG. 1
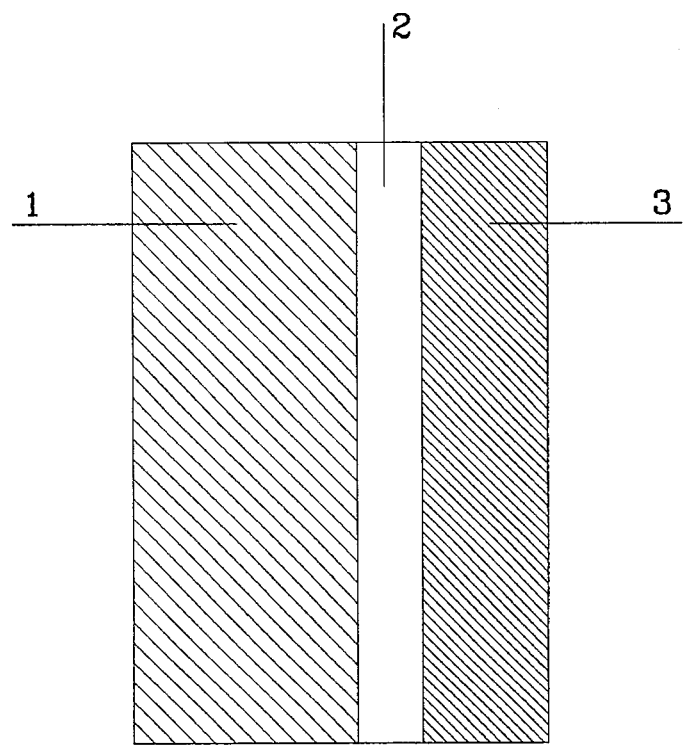
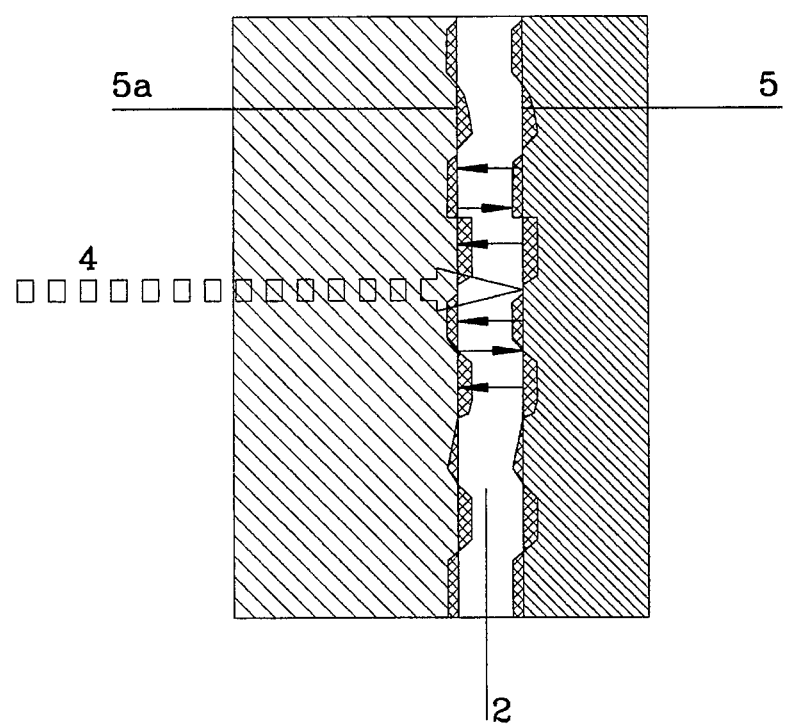

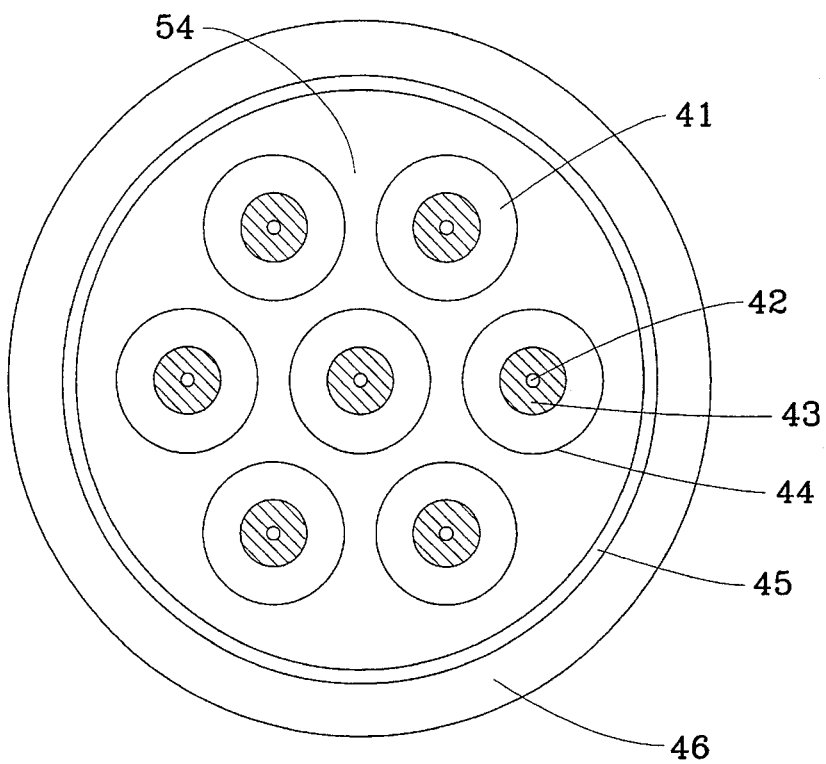
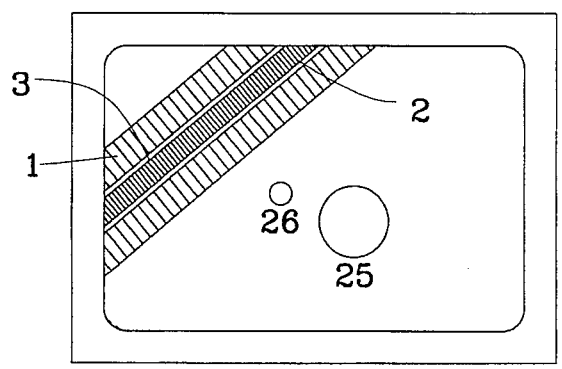
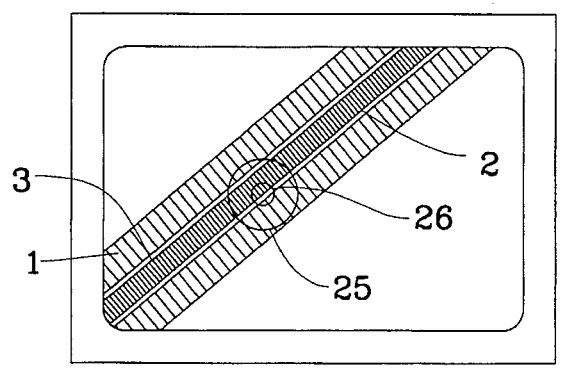

SYSTEM, METHOD AND APPARATUS FOR TREATMENT OF DEGENERATIVE BONE

FIELD OF THE INVENTION

This invention relates to a process and device for treatment of painful or degenerative changes in human or animal bones. More particularly, the invention relates to a such a process and device for changes which have caused a gap to form between two boundaries surfaces, with a distance of less than 5 millimeters separating the bone from an acoustically "hard" body such as an implant, bone, tooth and the like. The invention relates specifically to use of focused acoustic shock waves to set into vibration the soft tissue such as connective tissue, fat and the like, in the gap between the boundary surfaces, such as the surface of the bone and the surface of another acoustically hard body.

BACKGROUND OF THE INVENTION

A device for the mechanical stimulation of body parts with damaged bones is suggested in the Article "Controlled Mechanical Stimulation in the Treatment of Tibial Fractures" by J. Kenwright, et al. *Clin. Orthop.* and Related Research, Vol. 241, pp. 3647, 1989.

It is also known from European Patent No. 450,423 (Clasbrummel) that certain parts of the body can be held in an external immobilization device and that a lesion area can thus be treated with stimulating, rhythmic, back-and-forth motions at a certain stimulational amplitude. Here the mechanical energy is supplied more-or-less directly to the fracture gap by means of a drive acting on the external immobilization device.

Devices for producing focussed shock waves are known from U.S. Pat. No. 2,559,227.

Shock waves are acoustic waves with a frequency spectrum ranging from audible frequencies to the ultrasonic (100 MHz). They are usually generated in water and conducted into the body of a human being or animal through a certain volume of water. Shock waves are known from various applications for the crushing of body concretions and from uses involving the induction and stimulation of bone growth. W. German Patent No. 2,351,247 and U.S. Pat. No. 4,905,671 are two such disclosures.

Shock waves can be produced by various technical generation processes; for example, the electrohydraulic process uses a spark discharge to generate the underwater shock waves. An elliptical metal reflector is used to focus the shock waves. The spherical underwater shock wave generated at the first focal point by spark discharge with an electrode is transmitted to and focussed at the second focal point of the semi-ellipsoid by reflection from the ellipsoid wall. For the purpose of therapy, imaging processes such as ultrasound or audiograph are used as a location aid so that the tissue to be treated can be made to coincide with this focus as discussed in U.S. Pat. No. 2,559,227. Another method by which shock waves can be produced and focussed is that based on the electromagnetic principle, according to which the shock wave is produced by a flat membrane and possibly focussed by means of an acoustic lens as shown in European Patent No. 183,236.

A second electromagnetic principle makes use of a cylindrical source in which case focussing is accomplished by means of a parabolic reflector disclosed in German Patent No. 4,036,981.

According to yet another principle of generation, the shock waves are produced by piezoceramic elements on a self-focusing spherical shell, taught by West German Patent No. 4,000,362.

OBJECTS OF THE INVENTION

The object of the invention is to develop a process for the treatment of boundary surface gaps between a bone and another acoustically reflective body such as an implant, a tooth, another bone fragment and the like.

Another object of the invention is to develop a process which brings about rapid closing and filling of the boundary surface gap with bone tissue.

Other objects will appear hereinafter.

SUMMARY OF THE INVENTION

The invention pertains to a process and a device for the treatment of painful or degenerative changes in human or animal bones which have caused a gap with a width of less than 5 mm to form at the boundary surface or interface between the bone and an acoustically reflective surface such as an implant, a tooth, or a bone fragment. A surface to be treated is located, for example using an x-ray machine or ultrasound device, and acoustic waves are focussed on that surface to produce improved results when compared to the use of acoustic machines without a locating device.

BRIEF DESCRIPTION OF THE DRAWINGS

FIG. 1 is a schematic illustration of two conditions for a bone structure with gap in front of implant;

FIG. 8 is a schematic view, shown in cross section, of the energy feed cable.

FIG. 11 is a schematic view of the x-ray monitor image before positioning.

FIG. 12 is a schematic view of the x-ray monitor image after positioning.

DETAILED DESCRIPTION OF THE PREFERRED EMBODIMENT

Figure 2:
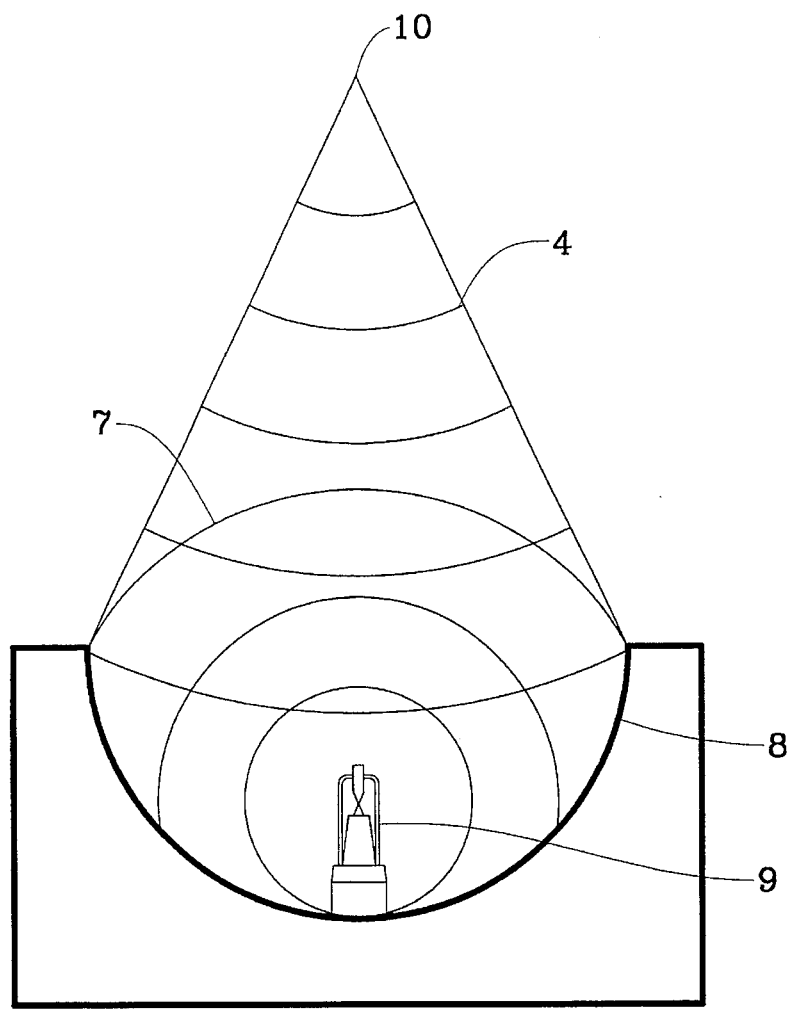
FIG. 2 is a schematic view of generation and focussing of shock waves.
Figure 5:
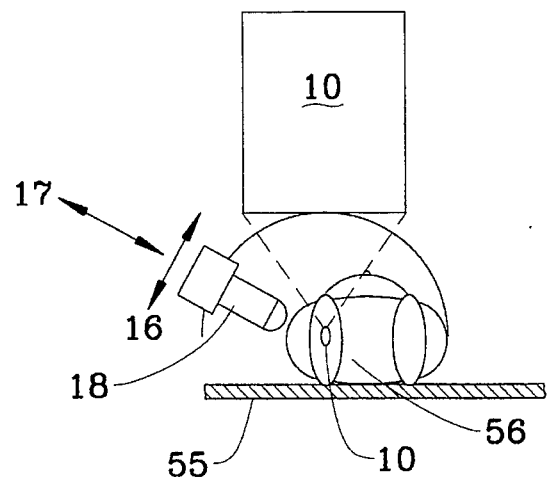
FIG. 5 is a schematic view of a device with an ultrasound locating machine.
Figure 3:
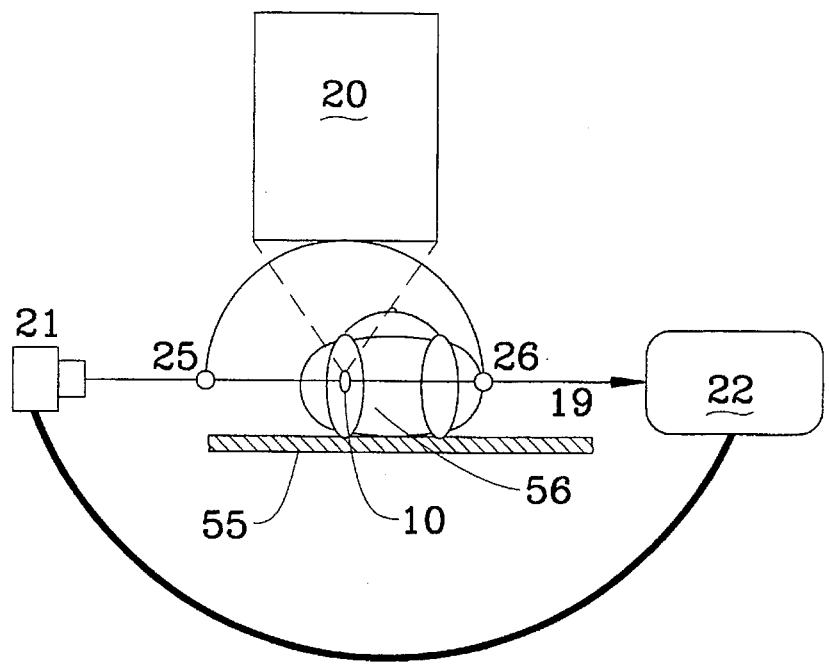
FIG. 3 is a schematic view of the combination system device with x-ray machine in a C-shaped configuration using a lateral projection.

The surface of an acoustically reflective body such an implant, bone or tooth, is located by means of a locating device shown as elements 21 and 22 in FIG. 3, and element 18 in FIG. 5, for example. The focal point for a source of focused acoustic waves 10, shown in FIG. 2, is adjusted by means of a control device in such a way that the focus is at least essentially on the boundary surface 5 of an acoustically reflective body 3.

FIG. 1 represents a bone structure with a gap in front of an implant. Gap 2 exists between an acoustically reflective bone or compacta 1 and the acoustically reflective body 3. On surface 5 of body 3, the incident acoustic compression and tension waves shown by arrow 4 bring about longitudinal, transverse and surface vibrations of a wide variety of frequencies and amplitudes. These vibrations propagate in the boundary surface gap 2 perpendicularly between the surface 5a of the bone and the surface 5 of the acoustically reflective body. Thus, a therapeutic effect is exerted.

In order to implement this process, a therapy head 20, shown in many of the figures is employed for generating focusably acoustic shock waves, such as shown in FIG. 2, where the waves 4 extend to a focal point 10. In the preferred embodiment, the therapy head 20 is equipped with a targeting device 25, 26. This targeting device is used preferably in connection with an x-ray machine as a locating aid, with two moveable targets being connected mechanically to the therapy head such that the pair of targets 25, 26 rotate around at least two different axis 23, 24, with an imaginary connecting line 19, 19a, shown, for example in FIGS. 3 and 4 respectively. The imaginary line 19 or 19a always extends between the two targets 25, 26 or 25a, 26a and, importantly, throughout the focal point 10 of the shock waves.

Figure 6:
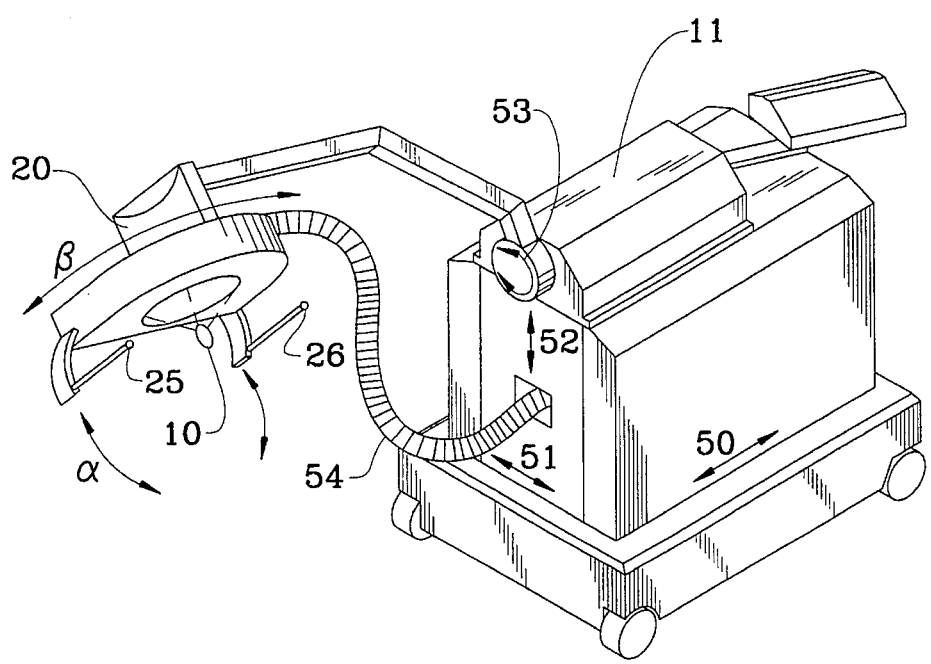
FIG. 6 is a perspective view of the device with directions of movement.

In FIG. 5, an alternative embodiment is shown using an ultrasound locating unit 18 for positioning the shock wave focus point 10 in the gap 2 between the patient's bone 1 and the acoustically reflective object 3. Ultrasound locating units 18 are known in other medical procedures. It is preferred that the unit 18 operate according to the B-image process such that a two dimensional cross-section is produced. The location of the boundary surface gap 2 is located by adjustment of the cross-section so that it is concentric with the shock wave focus point 10. This is accomplished by moving the scanner 18 around a spherical surface 16 in the direction shown in FIG. 5 by the arrow. To further ensure that the ultrasonic transmitter 18 can be acoustically coupled to the skin of the patient, the scanner will also need to be moved axially with respect to the shock wave, i.e., in the direction shown by arrow 17. The ultrasonic imaging process is then carried out in a conventional manner to produce x, y and z coordinates as shown in FIG. 6 by arrows 50, 51 and 52, so that the device 11, which is on wheels, can be moved to position it so that the shock wave focal point 10 will coincide with the gap 2 in the patient.

Turning again to FIGS. 1 and 2, the shock wave 4 is radiated as a compression wave with a tension component of less than 20% of the maximum pressure amplitude through the surface of the skin and into the body of the patient. As wave 4 travels through the intermediate layers of tissue, those properties being similar to those of water in terms of density, sonic speed and the like, the wave 4 undergoes only slight attenuation before reaching the periosteum. After the shock wave passes throughout the periosteum, it arrives at the compacta 1, which itself is acoustically reflective. This compacta differs from the water like soft tissues because of a much greater density and higher sonic speed capacity. The shock wave is thus damped in this acoustically reflective tissue, with the result that some of the energy is absorbed over a distance of a few centimeters. When the sound wave strikes a metal implant or some other acoustically reflective body 3, the sound wave is reflected and travels back again as a compression wave 6.

If, as the result of stress or biological repair processes, direct contact with the bone surface of an implant or tooth has changed and a boundary surface gap 2 has formed, where, for example, fat and infiltrations and borders of connective and fibrogenic tissue have been observed, or if a fracture gap is present between two bone fragments, there are two more physical boundary surfaces 5, and 5a, shown in FIG. 1. A shock wave emerging from the compacta 1 or spongiosa 5a penetrates as a tension wave into the boundary surface gap 2 in front of the acoustically reflective body 3, whether it is an implant, bone or tooth or the like. In comparison to the bone in front, gap 2 represents an acoustically soft tissue. Thus, a shock wave component is formed by phase transformation into a tension wave under acoustically "soft" condition.

These tension waves are then reflected in an acoustically "hard" manner from acoustically reflective body 3 in the same way as the compression waves, and thus, travel back as tension waves to the compacta/spongiosa of bone 1. Since this material is also acoustically hard in comparison to the tissue or fat in boundary surface gap 2, this means that the wave is also reflected back by this surface of the bone. Accordingly, in the gap of volume, the tension wave components are superimposed by multiple reflections depicted by the arrows in the lower portion of FIG. 1. If the gap 2 is small enough, such as less than 5 millimeters, temporary standing waves form in the boundary surface gap by a superimposition and by the vibration of the two boundary surfaces. These standing waves vibrate in various modes and amplitudes, as shown in the lower portion of FIG. 1.

The temporary standing waves and the superimposition of the tension wave components act therapeutically by transforming undifferentiated cells; by bringing blood into the gap with the resulting catabolic and anabolic processes; by drawing bone splinters or microfractures into the gap, which then serve as nucleation seed for the process of osteogenesis; and exerting tensile and compressive mechanical stress on the boundary surfaces, whereupon these surfaces also react with osteogenesis. The machine 11 shown in FIG. 6 contains a device 20, such as that shown in FIG. 2, for generating a shock wave 4. One device suitable for generating such a shock wave is shown in U.S. Pat. No. 2,559,227. In this reference, a spark gap 9 and a semi-ellipsoid 8 generate an underwater shock wave to produce the shock wave 4 as shown in FIG. 2.

Figure 4:
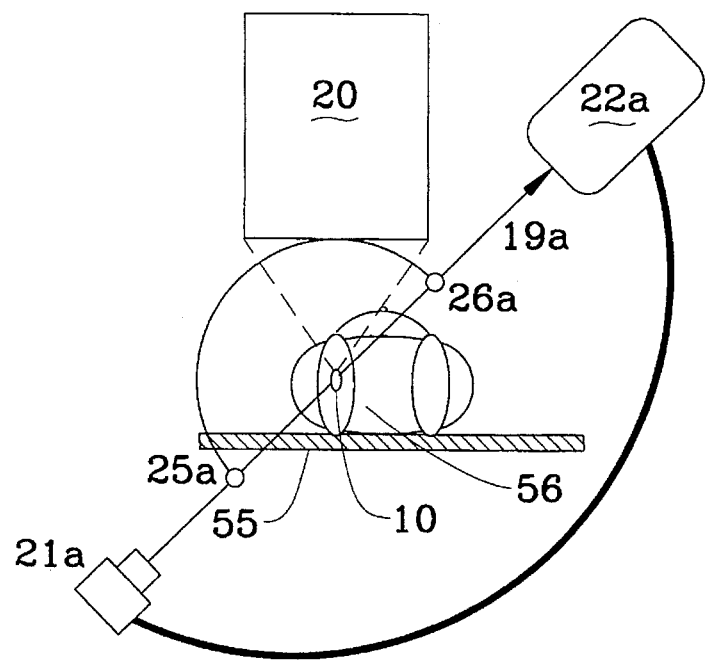
FIG. 4 is a schematic view of this system device with x-ray machine in a C-shaped configuration of a 45° projection.
Figure 7:
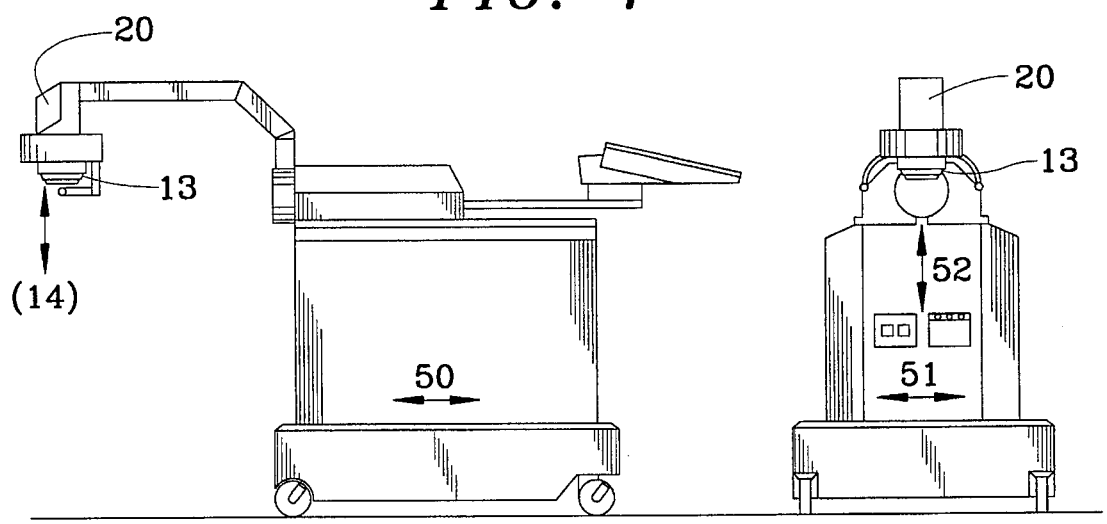
FIG. 7 is a side and front view of the device with directions of movement.

The shock wave 4 is shown through a volume of water to the patient, such as a water cushion coupling element 13, shown in FIG. 7, for resting on the surface of the patient's skin as shown in FIGS. 3, 4 and 5. A focal point $F_2$, not illustrated, represents therapeutic center focal point 10 which, of course, is located outside or inside the water cushion 13. As shown in FIG. 7, water cushion 13 can be moved in the direction of arrow 14 to reorient the focal point 10 and align the acoustic shock wave energy with the appropriate portion of the surface of the body of the patient.

The therapy head generically described herein, consists of an surface 8 and electrode 9, as shown in FIG. 2, and also includes water cushion 13. It can move in space in x, y and z directions 50, 51 and 52, as well as in rotational directions shown by arrow 53 in FIG. 6. Thus, the device is positionable to treat various and different areas of the human body from various directions. This is particularly useful in treatments where the patients have been anesthetized, because then there is no need to move the patient.

The electrical energy being transmitted from the high voltage generator electrode 9 is supplied by means of as flexible conductor 54 so that the therapy head 20 may be a small, light and mobile as possible. Of course, energy feed line 54 is designed to operate with a minimum of inductance to ensure that shock waves may be produced rapidly. Some energy feed lines employ coaxial conductors, which, given the amount of energy to be transmitted and the low inductance desired, are therefore quite bulky and rigid, and thus undesirable.

The present invention provides a solution to this problem for energy feed line 54 through the use of a plurality of thin, flexible coaxial cables, shown in FIG. 8 as cables 41, which are arranged in parallel both mechanically and electrically. Shown in FIG. 8 is an energy feed line 54 with 7 coaxial cables. The cable 54 includes an outer insulation layer 46 and an inner metallic shielding 45. The individual coaxial cables 41 each include a metallic external conductor 44, an insulation layer 43 and an inside conductor 42. This cable is admirably suited to the present invention, as it is capable of providing minimum inductance and maximum energy, and has nether the rigidity nor the bulk of conventional cables. There also could be an additional insulation layer around the external conductor 44.

In operation of the present invention, the gap 2 which is to be treated is located by the imaging processes using ultrasound 18 or by the x-rays 21, 22. The therapy head 20 is positioned relative to the portion of the body 56 to be treated, so that gap 2 of FIG. 1 coincides with the therapeutic focus volume or focal point 10. In order to accomplish this with x-rays, a unique locating device 25, 26 is employed with a standard x-ray machine 21, 22 for accurate and easy positioning of the therapy head 20.

Figure 9:
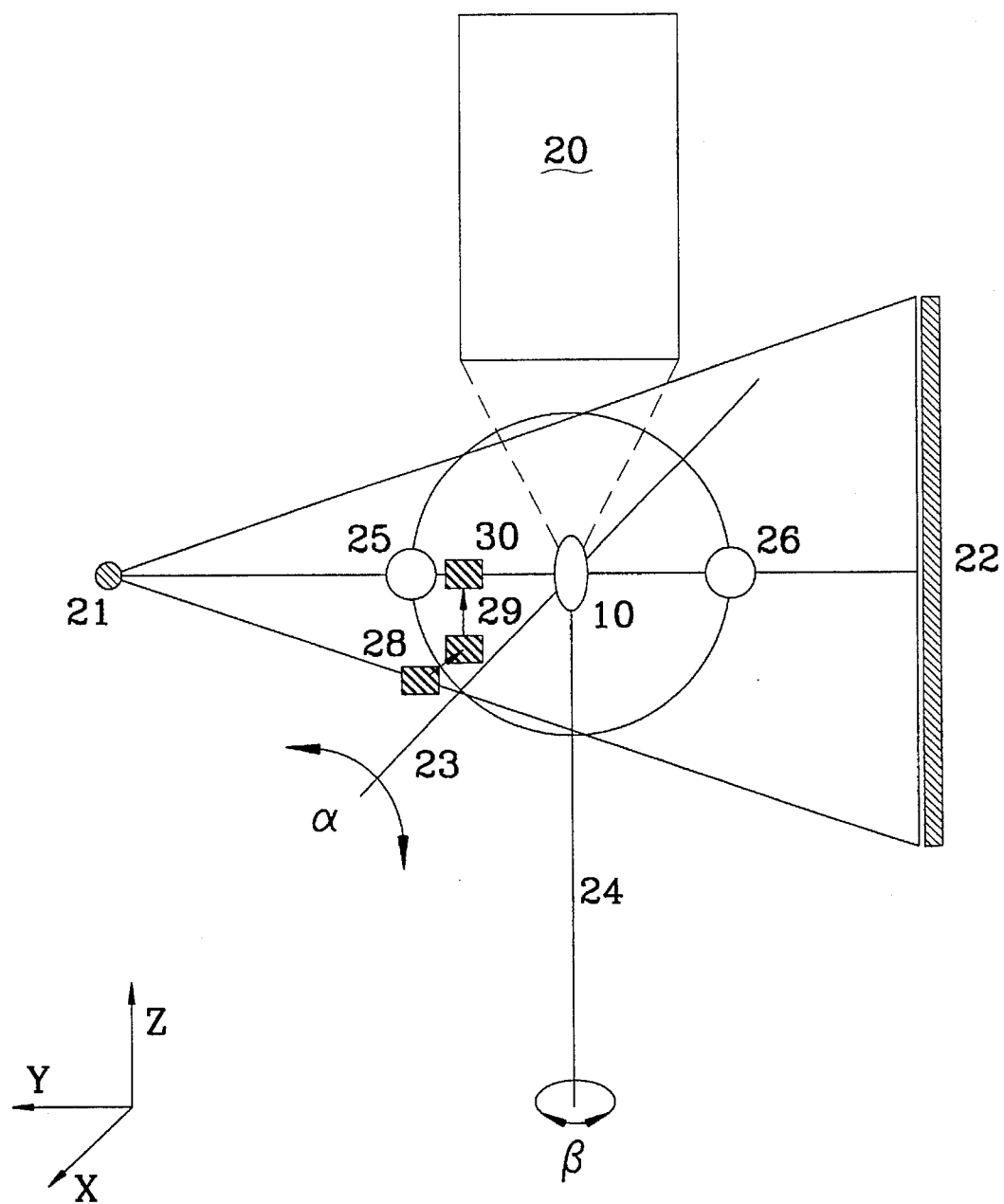
FIG. 9 is a schematic view showing the projection of the x-ray locating and positioning system in a lateral projection.
Figure 10:
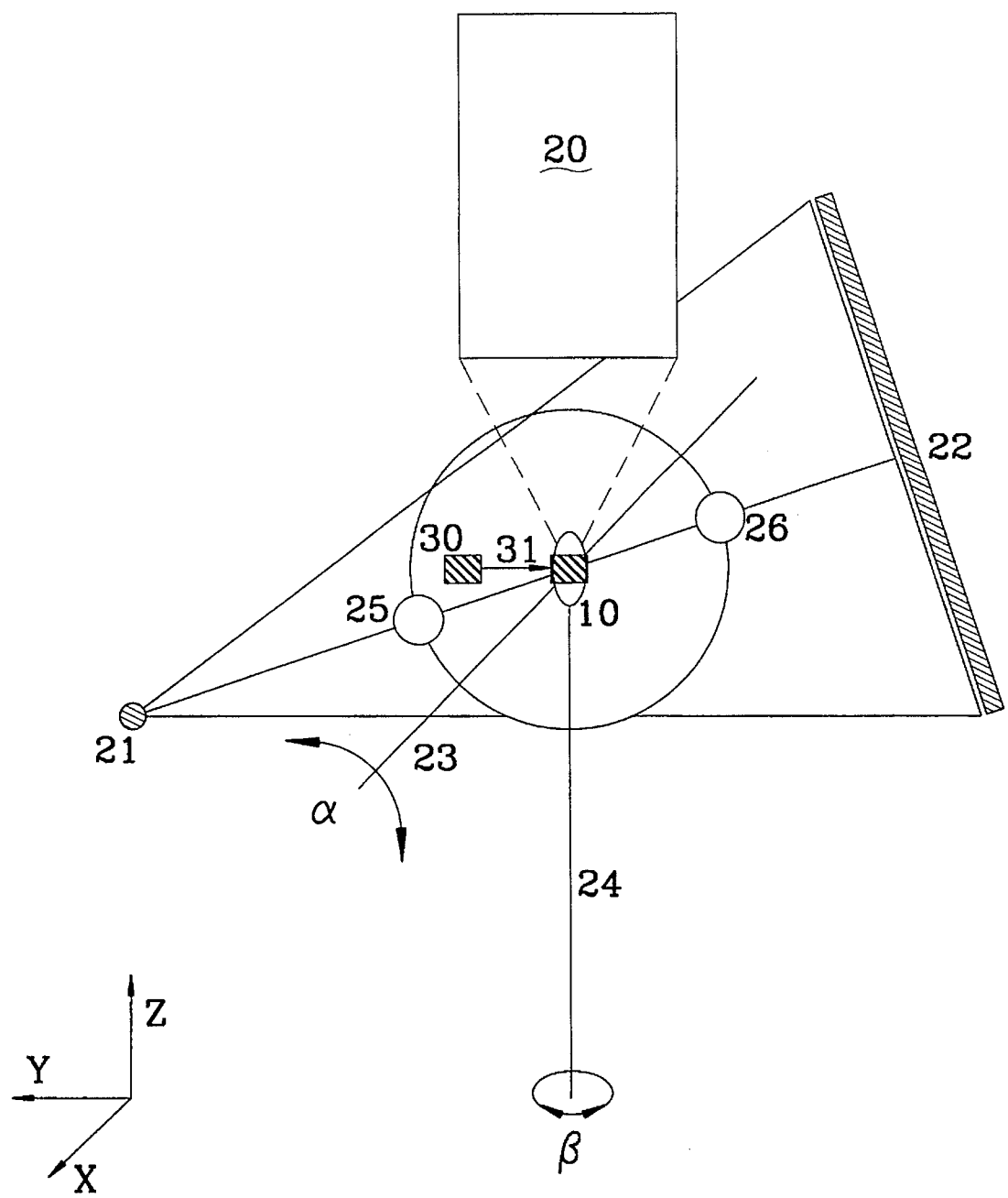
FIG. 10 is a schematic view illustrating the projection of the x-ray locating and positioning system at a 30° projection.

FIGS. 9 through 12 show the operation of the present invention using the x-ray unit described above. Specifically, preliminary locations of gap 31, labelled 28, 29 and 30 in FIG. 9, are not aligned with the focal point 10 of the therapy head 20. Movement in the x,y,z direction, as well as rotation about axis 23 and 24 as shown by angles α and β, permits alignment of, for example, gap 31 as shown in FIG. 10 by causing coincidence of focal point 10 on the line between locating device 25, 26. As can be noted, the x-ray machine provides an x-ray between source 21 and plate 22 which passes through the targets 25 and 26 to define an axial line 19 on which it can be determined the gap 31, for example, has been aligned. This alignment can be achieved by subjecting a particular gap, such as gap 31, to the above x-ray location process from various directions. Using all three space coordinates, focal point 10 coincides quickly and easily with the gap to be treated, as described in greater detail hereinafter.

The therapy head 20 is positioned by moving part of the overall machine in the x-y plane, also by raising and lowering the machine in the z direction, and further by rotating the entire machine around the z-axis and by rotating the arm carrying the therapy head in the direction shown by arrow 53 of FIG. 6. Instead of raising and lowering the machine in the Z-direction it is also possible to move the patient by means of a patient stretcher in the Z-direction.

The locating and positioning steps described above are carried out in a sequence of identical steps, in which each actual path 50, 51, 52 and 53 travelled by the treatment unit 11 depend on the first projection angle of the x-ray unit 21, 22. FIGS. 3 and 4 show the combination of therapy head 20 and the x-ray machine with its C-shaped configuration x-ray source 21, 21a and image amplifiers 22 and 22a. In FIG. 3, focal point 3 has yet to be positioned on boundary surface 2 which is to be treated. The patient 56 is lying on a table 55 which also can be moved in the x,y and z directions. It is particularly advantageous for the table 55 to be adjustable in at least the z direction to permit the patient to easily climb on to the table.

The path of x-ray beam being emitted 21 is aligned as closely with the horizontal as possible and also in the direction of y-axis 51 of device 11. The result is that the x-ray beam is projected in direction 19, shown in FIG. 3. By making appropriate adjustments to the C-shaped x-ray machine 21, 22 and the patient table 55, the gap to be treated is brought into the approximate center of the x-ray image being projected by the x-ray machine, to appear on a t.v. monitor as illustrated in FIGS. 11 and 12.

The projection and location process and movement of the therapy head are shown as an example. Initially, the therapy focal point 10 is moved in the x and z directions onto gap 2 which is to be treated. The device is then adjusted in such a way by rotation of target 25,26 around axis 23 and 24, through angles α and β such that the two targets 25, 26 coincide with projection beam 19 and the gap 2 which is to be treated. This adjustment of the x and z directions appears on the x-ray monitor as indicated in the difference between FIGS. 11 and 12. After the adjustment is appropriately made, an image such as that shown in FIG. 12 appears on the x-ray monitor. Note that both target mark 25 and target mark 26 coincide with the gap 2 which is to be treated. Thus, both the x direction and the z direction of treatment focal point 10 have been set. Returning back to FIG. 9 illustrates a detailed version of the adjustment process where gap 2 is now labeled 28. 28 is first moved in the x direction to position 29 and from there in the z direction to position 30, with the result that the x-ray projection produces the monitor image shown in FIG. 12.

The conclusion of the adjustment procedure involves adjustment of the y coordinate. It is advantageous to move in the direction in which the C-shaped x-ray machine projects its beam over an angle greater than 30°, from 21 to 21a and from 22 to 22a. Accordingly, the new projection line shown in FIG. 4 is labeled 19a. With projection direction 19a, the targeting device is now rotating around axis 23 and 24 into positions 25a and 26a. Because the x direction 50 and the z direction 52 have already been set, the only adjustment needed is the y axis 51. Thus, the gap area moves from position 30 to position 31 shown in FIG. 10. The x-ray monitor in FIG. 12 now shows, after the adjustment, the superimposition of gap 2 with targets 25 and 26. After this adjustment procedure, shock wave focal point 10 is made to correspond with gap 2 as intended for therapy, and the treatment with the shock waves may begin.

Treatment may require a number of shock waves, from more than 100 to more than 10,000. Intensity of the shock waves may range from more than 20 to more than 2,000 bars, at a frequency more than 10 to more than 600 shock waves per minute. This treatment may be repeated from 1 to 25 times in order to be effective.

While various embodiments of the present invention have been shown, one skilled in the art will appreciate that various modifications, substitutions, changes and omissions may be made without departing from the spirit of the present invention. Accordingly, it is intended that the scope of the present invention may be limited only by the scope of the following claims:

What is claimed is:

1. A process for exposing a patient with acoustic shock waves generated by a therapy head and conducted through the surface of the skin and into the body of the patient comprising the steps of locating a boundary surface gap between bone and an acoustically reflective body by using a locating device comprising an x-ray beam imaging system and two moveable targets connected mechanically to the therapy head and by causing the focal point of the shock waves to coincide with an imaginary connecting line extending between the two targets; and focussing the shock waves in that part of the gap small enough to cause reflections of the focussed shock waves to generate vibrations in the bone surfaces, the surfaces of the acoustically reflecting body and in the volume of the boundary surface gap.

2. The process of claim 1 wherein said locating of the boundary surface gap is accomplished by first positioning said locating device to fix two coordinates of the focal point and thereafter positioning said device in a second location to adjust the third coordinate.

* * * * *